United States Patent [19]

Hermes

[11] Patent Number: 5,424,136
[45] Date of Patent: Jun. 13, 1995

[54] POLYMERS OF 1,3 DIOXOLAN-4-ONES

[75] Inventor: Matthew E. Hermes, Easton, Conn.

[73] Assignee: United States Surgical Corporation, Norwalk, Conn.

[21] Appl. No.: 903,373

[22] Filed: Jun. 24, 1992

[51] Int. Cl.$^6$ .............................................. B32B 27/42
[52] U.S. Cl. .................................. 428/524; 528/220; 528/226; 528/228; 528/361; 525/471; 525/535; 525/540; 428/423.1; 428/425.8
[58] Field of Search ............... 528/220, 226, 228, 361; 525/471, 535, 540; 428/423.1, 425.8, 524

[56] References Cited

U.S. PATENT DOCUMENTS

| | | | |
|---|---|---|---|
| 3,169,945 | 2/1965 | Hostettler et al. | 528/355 |
| 3,301,824 | 1/1967 | Hostettler et al. | 528/354 |
| 4,348,322 | 9/1982 | Edwards et al. | 549/296 |
| 4,447,625 | 5/1984 | Kunz | 549/265 |
| 4,603,695 | 8/1986 | Ikada et al. | 128/334 |

OTHER PUBLICATIONS

Pentti Salomaa, et al., The Kinetics and Mechanisms of the Uncatalyzed and Acid-Catalyzed Hydrolysis of 1,3–Dioxolones–(4) and Its Methyl Derivatives. part I. Dioxolones Derived from Formaldehyde, Acta Chem. Scand. (1963) 17: 103–110.
V. V. Pchelintsev, et al., Kinetic Principles and Mechanisms of Hydrolytic Degradation of Mono- and Polyacetals–A Review, Polymer Degradation and Stability (1988) 21: 285–310.
Wayne R. Sorenson, et al., Preparative Methods of Polymer Chemistry, Interscience Publishers Inc., N.Y., pp. 239–244.
Ring Opening Polymerization, Encyclopedia of Polymer Science 12, pp. 36–42, John Wiley & Sons, N.Y., 1988 Farines, et al., Etude de dioxolanones-4: Synthese et proprietes physiques: Bulletin De La Societe Chimique De France, 1970, No. 1 pp. 332–340.
CA115(6):51178q.
CA104(15):129820n.

*Primary Examiner*—Samuel A. Acquah

[57] ABSTRACT

Useful materials are formed by polymerizing a 1,3 dioxolan-4-one monomer. The 1,3 dioxolan-4-one monomer can be copolymerized with a variety of comonomers, including glycolide, lactide, dioxanone, trimethylene carbonate and caprolactone.

20 Claims, No Drawings

POLYMERS OF 1,3 DIOXOLAN-4-ONES

FIELD OF THE INVENTION

This invention relates generally to novel polymer compositions. More specifically, this invention relates to homopolymers and copolymers made from 1,3 dioxolan-4-one monomers. The polymers are useful in making a variety of products, including medical devices such as bioabsorbable medical implants.

BACKGROUND OF THE INVENTION

A variety of synthetic bioabsorbable materials are known. For example, synthetic absorbable sutures and other medical devices made from polyglycolic acid, lactic acid, copolymers of glycolide and lactide, polydioxonone, trimethylene carbonate copolymers and caprolactone copolymers are known. See, for example, U.S. Patent Nos. 2,668,162; 2,703,316; 2,758,987; 3,225,766; 3,297,033; 3,422,181; 3,531,561; 3.565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4.234,775; 4,237,920; 4,300,565; 4,052,988; 4,243,775; 4,429,080; 4,705,820; 4,891,263; 4,916,193; 4,920,203; 4,788,979; 4,838,267; and 4,653,497.

The synthesis and properties of 1,3-dioxolan-4-one and substituted 1,3 dioxolan-4-one compounds have been described by Farines et al. (Bull. Soc. Chim. France, 1, 1970, 332–340). The kinetics and mechanisms of the uncatalyzed and acid-catalyzed hydrolysis of 1,3-dioxol-4-one and its methyl derivatives have been studied by Salomaa et al., Acta. Chem. Scand. 17 (1963) pp. 103–110. The disclosure of these two documents are incorporated herein by reference.

Applicant is unaware of any teaching in the prior art of the formation of polymers of 1,3 dioxolan-4-ones or the use of such polymers in the manufacture of medical devices, such as medical implants.

SUMMARY OF THE INVENTION

It has been found that useful polymer products can be formed by polymerizing a 1,3 dioxolan-4-one monomer, that is, a monomer having the following general formula:

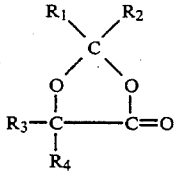

wherein $R_1$, $R_2$, $R_3$, and $R_4$ are the same or different and are individually selected from the group consisting of hydrogen, halogen and essentially hydrocarbon groups. $R_1$ and $R_2$ may be separate groups or intramolecularly bonded to form a cyclic group. $R_3$ and $R_4$ may likewise be separate groups or intramolecularly bonded to form a cyclic group.

The compositions of the present invention may be homopolymers of a 1,3 dioxolan-4-one monomer, or may be a copolymer, either of different 1,3 dioxolan-4-one monomers or of a 1,3 dioxolan-4-one monomer with one or more comonomers capable of forming biocompatible polymers. Such comonomers include, for example, glycolide, lactide, caprolactone, dioxanone and trimethylene carbonate. Other suitable comonomers include N-caboxy anhydrides, anhydro sulfites, oxazalines and morpholine diones. The compositions of this invention may be random or block copolymers.

The polymer and copolymer compositions of this invention can be formed into a variety of products, including medical devices, and are particularly well suited for bioabsorbable implantable medical devices.

DESCRIPTION OF PREFERRED EMBODIMENTS

The materials of the present invention are formed by polymerizing a 1,3 dioxolan-4-one monomer. Suitable 1,3 dioxolan-4-one monomers will have the following general formula:

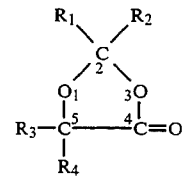

wherein $R_1$, $R_2$, $R_3$ and $R_4$ are the same or different and are individually selected from the group consisting of hydrogen, halogen and essentially hydrocarbon groups. $R_1$ and $R_2$ may be separate groups or intramolecularly bonded to each other to form a cyclic group. Similarly, $R_3$ and $R_4$ may be separate groups or intramolecularly bonded to each other to form a cyclic group.

By the phrase "essentially hydrocarbon" it is meant that the groups $R_1$–$R_4$ may contain hetero atoms provided they do inhibit polymerization to an unacceptable degree. Preferably, groups $R_1$–$R_4$ do not inhibit degradation of the polymer to an unacceptable degree and do not give rise to toxic or difficultly metabolizable degradation products.

Suitable essentially hydrocarbon groups for $R_1$–$R_4$ include alkyl, alkenyl, alkynyl, cycloalkyl and heteroalkyl or cycloheteroalkyl (containing, for example, oxygen atoms or nitrogen atoms).

Processes for the preparation of monomers useful in producing the polymers of the present invention are known. Generally speaking, the 1,3 dioxolan-4-one monomer is produced by the reaction of an acid with an aldehyde or ketone. $R_1$ and $R_2$ are substituents contributed by the aldehyde or ketone and $R_3$ and $R_4$ are substituents contributed by the acid. Thus, referring to the general formula of the 1,3 dioxolan-4-one shown above, for example, 1,3 dioxolan-4-one (i.e., wherein $R_1$–$R_4$ are each H) may be prepared by boiling glycolic acid with excess formaldehyde or a formaldehyde precursor in a large volume of benzene. By substituting lactic acid or α-hydroxyisobutyric acid for glycolic acid one produces 5-methyl-1,3-dioxolan-4-one and 5,5-dimethyl-1,3-dioxolan-4-one, respectively. By reacting glycolic acid with cyclohexanone, 2-cyclohexyl-1,3-dioxolan-4-one is produced. The preparation of other 1,3 dioxolan-4-one compounds is described in the Farines et al. article previously mentioned. As set forth therein, another acid suitable for use in producing the 1,3 dioxolan-4-one monomer include mandelic acid which produces a 1,3 dioxolan-4-one having the following structure when reacted with formaldehyde:

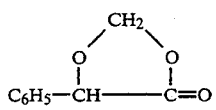

Aldehydes and ketones suitable for use in producing the 1,3 dioxolan-4-one monomer include acetaldehyde, propionaldehyde, acetone, cyclopentanone, 2-butanone, 4-methyl-2-butanone, and cyclohexanone. Useful formaldehyde precursors include trioxane and paraldehyde.

Monomers useful in this invention can also be prepared by reacting an acetal, such as methylal or ethylal, or cyclohexylhemiformal with methyl glycoate under acid conditions and distilling off the resulting alcohol. The following equation is representative of such a synthesis:

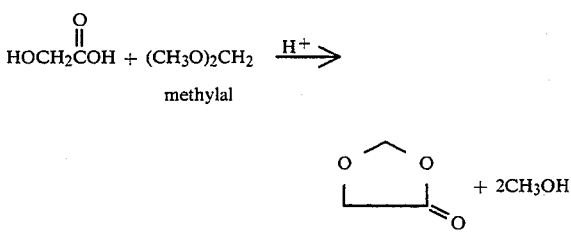

The polymers of this invention are prepared through ring opening polymerization of the 1,3 dioxolan-4-one monomer. Bulk or solution polymerization techniques can be employed. Polymerization can be achieved by heating the monomer in a suitable reaction vessel under a nitrogen atmosphere in the presence of an initiator and a catalyst. The temperature maintained within the vessel will vary depending upon the particular monomer employed but typically will be within the range $-20°$ to $300°$ C. In some cases, the temperature within the vessel should be maintained below a ceiling temperature of about $100°$ C. The polymerization time can range from about 2 to about 200 hours.

Catalysts useful in the polymerization of 1,3 dioxolan-4-one monomers will be cationic anhydrous catalysts. Suitable catalysts of this type include $SnCl_2$, Stannous octoate and antimony salts. Other useful catalysts are those described in connection with the polymerization cyclic carbonates in U.S. Pat. No. 3,301,824, which is incorporated herein by reference.

Suitable initiators may be selected from a large range of protonic and Lewis acids, amines and phosphines, hydrides, alkoxides, alkali derivatives of alkali and alkaline earth metals, and hydrogen-donor substances such as carboxylic acids, alcohols, glycols and alkanolamines. Other suitable initiators which may be employed include tetraalkylammonium carboxylate salts; products of the reaction of zinc or aluminum alkyls with water or alcohols; tin (II), tin (IV), and organoaluminum components such as trialkylaluminum (as shown in CA116(22):214954b); bimetallic oxoalkoxides, particularly of aluminum with zinc; and organometal compounds of graphite-alkali metal complexes alone or in combination with cryptands or crown ethers.

The polymerization reaction can be carried out in the presence of an inert normally-liquid organic vehicle, such as, for example, aromatic hydrocarbons, e.g., benzene, toluene, xylene, ethylbenzene, and the like; various oxygenated organic compounds such as anisole, the dimethyl and diethyl ethers of ethylene glycol, and the like; normally saturated hydrocarbons including the open chain, cyclic and alkyl substituted cyclic hydrocarbons such as hexane, heptane, various normally liquid petroleum hydrocarbon fractions, cyclohexane, the alkylcyclohexanes, decahydronaphthalene and the like. Mixtures of inert normally liquid organic vehicles can also be used.

As a homopolymer, the polymers of the present invention will have a repeat unit represented by the following general formula:

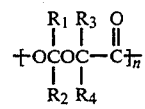

wherein $R_1$–$R_4$ are as defined above.

The physical characteristics of the polymers of this invention can be tailored by the choice of $R_1$–$R_4$. For example, the degree of crystallinity may be adjusted by incorporating different moieties for $R_1$–$R_4$. Thus, where $R_1$–$R_4$ are the same and are hydrogen, the crystallinity of the polymer would be such as to allow it to be spun into fibers. The incorporation of one or more methyl groups for one or more of $R_1$–$R_4$ may lower the crystallinity of the resulting polymer somewhat. Incorporating other groups for one or more of $R_1$–$R_4$ may lower the crystallinity of the polymer to the extent that it is no longer fiber-forming, but rather can be molded or cast into a useful form. The crystallinity of the polymer may also be adjusted by the choice of comonomer, if any, employed.

As another example, the rate of hydrolysis of the polymer can be adjusted by the selection of $R_1$–$R_4$. Thus, for example, polymers made from 1,3 dioxolan-4-one monomers which were prepared using formaldehyde as a reactant would have a relatively slow rate of hydrolysis. Generally, polymers made from 1,3 dioxolan-4-one monomers which were prepared using aldehydes as a reactant would have slower rates of hydrolysis compared to polymers made from 1,3 dioxolan-4-one monomers prepared from ketones. Additionally, the rate of hydrolysis may be adjusted by the choice of the acid used in preparing the 1,3 dioxolan-4-one monomer or by the choice of comonomer, if any, incorporated into the polymer.

The 1,3 dioxolan-4-one monomers may also be copolymerized with a variety of comonomers. Any comonomer which will result in a biocompatible copolymer may be used. Preferred comonomers are those which are presently used in the formation of synthetic absorbable medical devices. These include, for example, glycolide, lactide, dioxanone, trimethylene carbonate and caprolactone. Other suitable comonomers include N-carboxy anhydrides, anhydro sulfites oxazalines and morpholinediones. The copolymers of this invention, which may be random or block copolymers, can be prepared by using the same general conditions described above with respect to forming a 1,3 dioxolan-4-one homopolymer.

For example, the reactants may be placed into a suitable reaction vessel and heated, with or without reflux, in a nitrogen atmosphere under anhydrous conditions in the presence of a suitable catalyst, such as, for example, stannous octoate. As will be appreciated by those skilled in the art, the nature of the starting materials or their order of addition will dictate whether a random copolymer or block copolymer is produced.

The comonomers may be present in an amount ranging from about 1 to about 99 weight percent based on the total weight of the copolymer. Preferably, the copolymer will contain the comonomer in an amount from about 5 to about 95 weight percent based on the total weight of the copolymer. The amount of a particular comonomer employed may be chosen based upon the nature of the particular comonomer and the desired characteristics to be imparted to the material being produced. For example, by varying the amount of comonomer one may vary the rate at which the resulting product is absorbed by the body in which it is implanted. The strength of the resulting product and/or the flexibility of the resulting product can also be adjusted by the choice and amount of comonomer added, producing copolymers which range in their physical properties from brittle to elastomeric. It should be understood, of course, that combinations of two or more comonomers in varying amounts may be employed to provide a desired combination of characteristics in the material being produced.

In addition, the polymers of this invention can be melt blended with other polymers. The blend may then extruded into fibers or molded into useful products.

The polymers of the present invention are preferably bioabsorbable, either by hydrolysis or by enzymatic degradation.

The following non-limiting Examples illustrate how 1,3 dioxolan-4-one monomers and the polymers of the present invention can be made.

EXAMPLE 1

The parent member of the group, 1,3 dioxolan-4-one is prepared in low yield from formaldehyde and glycolic acid according to the procedure of Salomaa and Laiho, Acta. Chem. Scandanavia, 17,104(1963). These authors indicate yields of 1,3 dioxolan-4-one are limited because of polymerization of the formaldehyde present in the reaction system.

An improved procedure substitutes methylal (dimethoxymethane) for the formaldehyde. Glycolic acid (anhydrous), 2.28 g (0.03 mole) and methylal, 5.56 g (0.06 mole) and 0.2 g of p-toluenesulfonic acid are combined in a thick-walled polymer tube. The contents are cooled under nitrogen to −80 degrees Celsius and the tube is evacuated. The tube is sealed under vacuum and heated for 16 hours at 65 degrees Celsius.

The tube is cooled, and opened, the contents are dissolved in toluene and washed with a solution of sodium carbonate in water. The toluene solution is dried over anhydrous sodium carbonate then distilled carefully to remove unreacted methylal, methanol and toluene. The residual 1,3 dioxolan-4-one boils at 65 degrees Celsius at 16 Torr.

A second improved procedure substitutes cyclohexyl hemiformal for formaldehyde. Glycolic acid, 2.28 g (0.03 mole), cyclohexyl hemiformal, 7.8 g (0.06 mole) and p-toluenesulfonic acid, 0.2 g are charged to a polymer tube as above, cooled, evacuated and sealed. The contents are heated at 65 degrees Celsius for 16 hours. The tube is cooled, opened and the contents dissolved in methylene chloride. The methylene chloride solution is washed with a water solution of sodium carbonate, then dried over anhydrous sodium carbonate and distilled. Solvent is removed first, then 1,3 dioxolan-4-one is distilled from residual cyclohexanol.

EXAMPLE 2

5-Methyl-1,3-dioxolan-4-one is prepared by the method of Salomaa and Laiho or by following the procedures shown in Example 1 by substituting 2.7 g lactic acid for glycolic acid.

EXAMPLE 3

The 1,3 dioxolan-4-one monomers of Example 1 can be polymerized by adding 2.64 g (.03 mole) of the monomer, which had been previously purified and dried, to a reaction vessel containing 20 ml of dry toluene, in a nitrogen atmosphere. A solution of stannous octoate catalyst in diethylether is added to the reaction vessel to give 0.2 weight % catalyst. The reaction is maintained at 60° C. for 72 hours. Thereafter, the 1,3 dioxolan-4-one homopolymer can be recovered and purified using known techniques.

Similarly, a solution of aluminum triethyl in ethyl ether can be employed in this procedure in place of stannous octoate. Polymerization takes place in 96 hours at 25° C.

EXAMPLE 4

The 5-methyl-1,3-dioxolan-4-one monomer of Example 2 can be polymerized under the same conditions as set forth in Example 3 above.

EXAMPLE 5

A random copolymer of 1,3 dioxolan-4-one and 5-methly-1,3-dioxolan-4-one can be produced by adding the monomers of Examples 1 and 2 which have been previously dried to a reaction vessel and polymerizing under the conditions set forth above in Example 3.

EXAMPLE 6

A random copolymer of 1,3 dioxolan-4-one and glycolide can be prepared by simultaneously adding the monomer of Example 1 and glycolide, which have been previously dried to a reaction vessel and polymerizing under a nitrogen atmosphere using stannous octoate as a catalyst. The polymerization is allowed to proceed at 80° C. for 96 hours, at which time a random 1,3 dioxolan-4-one/glycolide copolymer is recovered. The copolymer is then subjected to heating under vacuum to remove unreacted monomer in accordance with known techniques.

EXAMPLE 7

A block copolymer can be prepared by first polymerizing 1,3 dioxolan-4-one as set forth in Example 3 and then, rather than recovering the homopolymer, adding 1.74 g (0.03 mole as glycolic acid) of previously dried glycolide and continuing to polymerize for an additional 96 hours at 80° C. The blocks of poly(1,3 dioxolan-4-one) and polyglycolide will be joined by the following linkages:

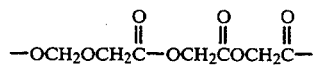

EXAMPLE 8

A block copolymer containing blocks of the random copolymers of Example 6 and blocks of a random glycolide/lactide copolymer can be prepared by first following the procedure of Example 6. Rather than recovering the copolymer product, however, a glycolide/lactide copolymer prepared by conventional techniques and thoroughly dried, is added to the reaction vessel and polymerization is allowed to continue for an additional 96 hours at 80° C.

The polymers of the present invention can be made into a wide variety of products in a wide variety of forms. For example, they can be molded or cast into any desired shape, drawn into fibers, cast as sheets and cut into a desired shape, or applied as a coating to either an absorbable or non-absorbable substrate. In addition, the polymers of this invention can be formed into degradable films for packaging applications. The fibers can be used as a monofilament, braided into a multifilament strand, or woven into a fabric or mesh, and may be combined with other absorbable or non-absorbable filaments. The following are Examples of how useful products may be formed from the polymers of the invention.

EXAMPLE 9

Filaments of the polymers of any of Examples 1 through 8 can be prepared as follows:

First, in order to determine the conditions for fiber production, samples of the polymer, dried under a flow of nitrogen (dew point $< -60°$ C.) are heated in the chamber of a capillary rheometer to a temperature above the melting point of the polymer. Monofilament samples are extruded at various temperatures and the viscosities are determined at these temperatures.

Dried polymer is then fed from a hopper designed to prevent contact of the polymer with atmospheric moisture, and extruded through a ¼" Killian extruder fitted with a gear pump and multifilament die. The temperature is chosen so that the viscosity of the melt is between 700 and 1200 sec$^{-1}$. Yarn is taken up over a lube godet and fed to a draw-frame. Speeds are adjusted to provide yarns with 10–50% elongation at break.

EXAMPLE 10

Molded products of any of the polymers from Examples 1 through 8 can be prepared by drying the resin under a flow of nitrogen at a temperature slightly above room temperature in a resin injection pot fitted to a molding machine. The polymer is molded at a temperature above the flow point into a desired shape. The molded product may then optionally be annealed to develop a desired degree of crystallinity. The molded product is then cooled and removed from the mold.

A wide variety of medical devices can be manufactured from the polymers of this invention. These include, but are not limited to, sutures, staples, clips and other fasteners, wound dressings, drug delivery devices, pins, screws and other implants.

What is claimed is:

1. A bioabsorbable copolymer made from a 1,3 dioxolan-4-one monomer.

2. A polymer as in claim 1 wherein said copolymer is a random copolymer.

3. A polymer as in claim 1 wherein said copolymer is a block copolymer.

4. A polymer as in claim 1 wherein said copolymer comprises one or more comonomers selected from the group consisting of glycolide, lactide, caprolactone, dioxanone, trimethylene carbonate, N-carboxy anhydrides, anhydrosulfites, oxazalines and morpholine diones.

5. A medical device comprising a bioabsorbable polymer of a 1,3 dioxolan-4-one.

6. A device as in claim 5 wherein said polymer is a homopolymer.

7. A device as in claim 5 wherein said polymer is a random or block copolymer.

8. A device as in claim 5 further comprising a non-absorbable component.

9. A device as in claim 7 wherein said copolymer is formed using a comonomer selected from the group consisting of glycolide, lactide, caprolactone, dioxanone, trimethylene carbonate, N-carboxyanhydrides, anhydrosulfites, oxazalines and morpholine diones.

10. A device as in claim 9 wherein said comonomer is present in an amount from about 5 to about 95 mole percent.

11. A device as in claim 5 wherein said 1,3 dioxolan-4-one polymer comprises a coating on the device.

12. A device as in claim 11 wherein said coating is applied to a non-absorbable component.

13. A medical device formed at least in part from a homopolymer or a copolymer made from one or more monomeric units selected from the group consisting of 1,3 dioxolan-4-one, 5-methyl-1,3-dioxolan-4-one, 5,5-dimethyl-1,3-dioxolan-4-one and 2-cyclohexyl-1,3-dioxolan-4-one.

14. A device as in claim 13 wherein said homopolymer or copolymer is in the form of a fiber.

15. A device as in claim 13 wherein said device is at least in part bioabsorbable.

16. A device as in claim 13 wherein said homopolymer or copolymer is bioabsorbable.

17. A device as in claim 13 wherein said medical device is an implant.

18. A device as in claim 5 wherein the 1,3-dioxolan-4-one is of the formula

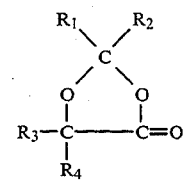

wherein $R_1$, $R_2$, $R_3$ and $R_4$ are the same or different and are individually selected from the group consisting of hydrogen and methyl.

19. A device as in claim 18 wherein polymer is bioabsorbable.

20. A device as in claim 18 wherein said polymer is a copolymer formed using a comonomer selected from the group consisting of glycolide, lactide, caprolactone, dioxanone, trimethylene carbonate, N-carboxyanhydrides, anhydrosulfites, oxazalines and morpholine diones.

* * * * *